(12) United States Patent
Fox et al.

(10) Patent No.: US 6,482,357 B1
(45) Date of Patent: Nov. 19, 2002

(54) TREATMENT OF AIRBORNE ALLERGENS

(75) Inventors: Rodney Thomas Fox, Cottingham (GB); Neale Harrison, Staffordshire (GB); John Farrell Hughes, Southampton (GB); Duncan Roger Harper, Hull (GB); Lindsey Faye Whitmore, Winchester (GB)

(73) Assignee: Reckitt Benckiser Limited, Slough (GB)

( * ) Notice: Subject to any disclaimer, the term of this patent is extended or adjusted under 35 U.S.C. 154(b) by 0 days.

(21) Appl. No.: 09/720,884

(22) PCT Filed: Jun. 23, 1999

(86) PCT No.: PCT/GB99/01976

§ 371 (c)(1),
(2), (4) Date: Jun. 8, 2001

(87) PCT Pub. No.: WO00/01429

PCT Pub. Date: Jan. 13, 2000

(30) Foreign Application Priority Data

Jul. 2, 1998 (GB) .............................................. 9814372

(51) Int. Cl.[7] ................................................. A61L 9/14
(52) U.S. Cl. .............................. 422/4; 239/3; 239/337; 239/690
(58) Field of Search ......................... 422/4; 239/3, 337, 239/690

(56) References Cited

U.S. PATENT DOCUMENTS

| | | | | |
|---|---|---|---|---|
| 4,110,427 A | * | 8/1978 | Kalat | 424/46 |
| 4,541,844 A | | 9/1985 | Malcolm | 55/10 |
| 4,680,173 A | * | 7/1987 | Burger | 424/47 |
| 4,718,920 A | | 1/1988 | Kinsey et al. | 55/10 |
| 4,766,515 A | | 8/1988 | Bollen et al. | 361/234 |
| 4,977,142 A | * | 12/1990 | Green | 514/23 |

FOREIGN PATENT DOCUMENTS

| | | | |
|---|---|---|---|
| EP | 0 168 243 | 1/1986 | A61L/9/00 |
| WO | WO 98/24356 | 6/1998 | A47L/13/40 |

* cited by examiner

*Primary Examiner*—Robert J. Warden, Sr.
*Assistant Examiner*—Sean E. Conley
(74) *Attorney, Agent, or Firm*—Fish & Richardson P.C.

(57) ABSTRACT

An improved method of denaturing or deactivating an airborne allergen comprising directing at the airborne source of the allergen liquid droplets from a spray device containing a liquid composition which includes an allergen denaturant or allergen deactivant, the improved method comprising imparting a unipolar charge to the said liquid droplets by double layer charging during the spraying of the liquid droplets by the spray device, the unipolar charge being at a level such that the said droplets have a charge to mass ratio of at leaset $\pm 1 \times 10^{-4}$ C/kg.

16 Claims, 4 Drawing Sheets

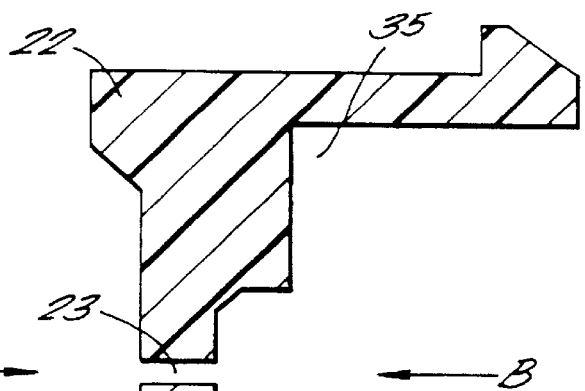
FIG. 3.
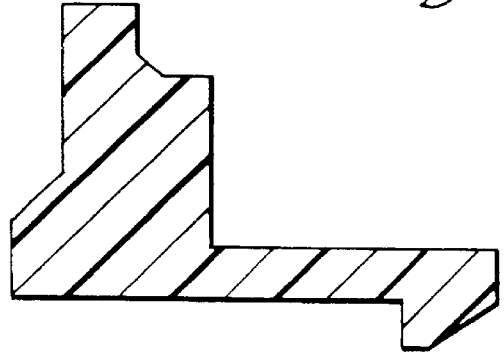
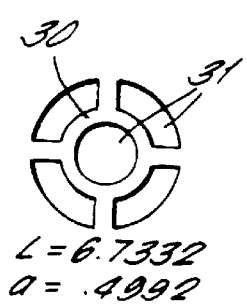
FIG. 4.
L = 6.7332
a = .4992
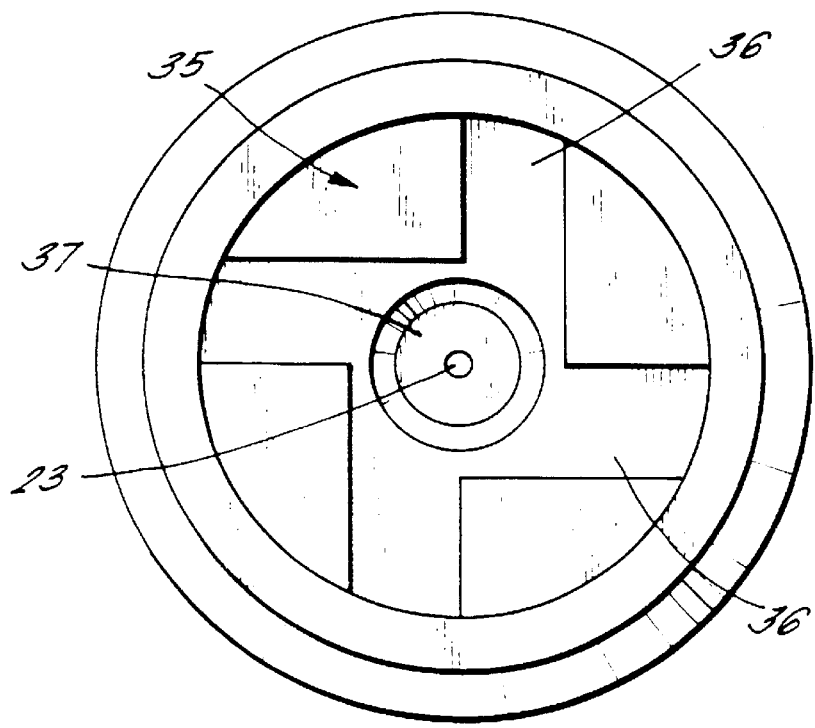
FIG. 5.

TREATMENT OF AIRBORNE ALLERGENS

The present invention relates to the treatment of airborne allergens.

BACKGROUND OF THE INVENTION

Various allergens are known which are transported through the air to trigger a human reaction. For example, it has been known for a long time that house dust can trigger allergenic reactions in humans, such as asthma and rhinitis. It was reported, as early as 1928 that it was the dust mites in the dust that were the primary source of the allergenic response, but it was only in the 1960's that researchers appreciated its significance.

It is believed that the faeces of the house dust mite, *Dermatophogoides farinae* (known as Der-f) and *Dermatophagoides pteronyssinus* (known as Der-p) trigger the immune response of the body, thereby giving rise to well known allergenic symptoms.

One way to overcome these allergenic responses has been to vacuum clean surfaces, such as carpets, that contain the dust mites and their faeces thoroughly and often, but that is both time consuming (it has to be regularly done to ensure an allergenic free environment) and is very dependant on the efficiency of the vacuum cleaner and filter bag used, e.g. micron filter bags or two layer vacuum bags.

An alternative method of creating an allergen-free environment has been to denature the allergen, for example, by using an allergen denaturant applied to airborne allergens by means of an aerosol spray device. Such a device produces an aerosol spray when activated and this spray may be targeted at any space which is to be treated.

The allergens to be treated are airborne particles and the use of a known aerosol spray device results in a low collision rate between the allergen denaturant and the airborne allergens. The practical consequence of such a low collision rate is that the allergen denaturant must be used in a high amount in order to be effective. There may be other consequences such as, in the case where the aerosol spray composition includes a perfume or fragrance, a strong perfume smell or a limited fragrance choice.

Other allergens which are problematic are cat allergens (Fel-d) and cockroach allergens (Bla-g). These can be denatured using an allergen denaturant for the specific allergen applied using an aerosol spray device.

An aerosol spray type device would be of improved efficiency if the spray droplets had a greater collision rate with the allergen particles and if the droplets could wet the surface of the allergen particles. We have now developed an improved method of denaturing or deactivating airborne allergens.

SUMMARY OF THE INVENTION

According to the present there is provided a method of denaturing or deactivating an airborne allergen comprising directing at the airborne source of the allergen liquid droplets from a spray device containing a liquid composition which includes an allergen denaturant or allergen deactivant, the method comprising imparting a unipolar charge to the said liquid droplets by double layer charging during the spraying of the liquid droplets by the spray device, the unipolar charge being at a level such that the said droplets have a charge to mass ratio of at least $+/-1\times10^{-4}$ C/kg.

BRIEF DESCRIPTION OF THE DRAWINGS

FIG. 3 is a cross section through the actuator insert of the assembly shown in FIG. 2;

FIG. 4 shows the configuration of the bore of the spraying head shown in FIG. 3 when viewed in the direction A;

FIG. 5 shows the configuration of the swirl chamber of the spraying head shown in FIG. 3 when viewed in the direction B.

DETAILED DESCRIPTION

Figure 1:
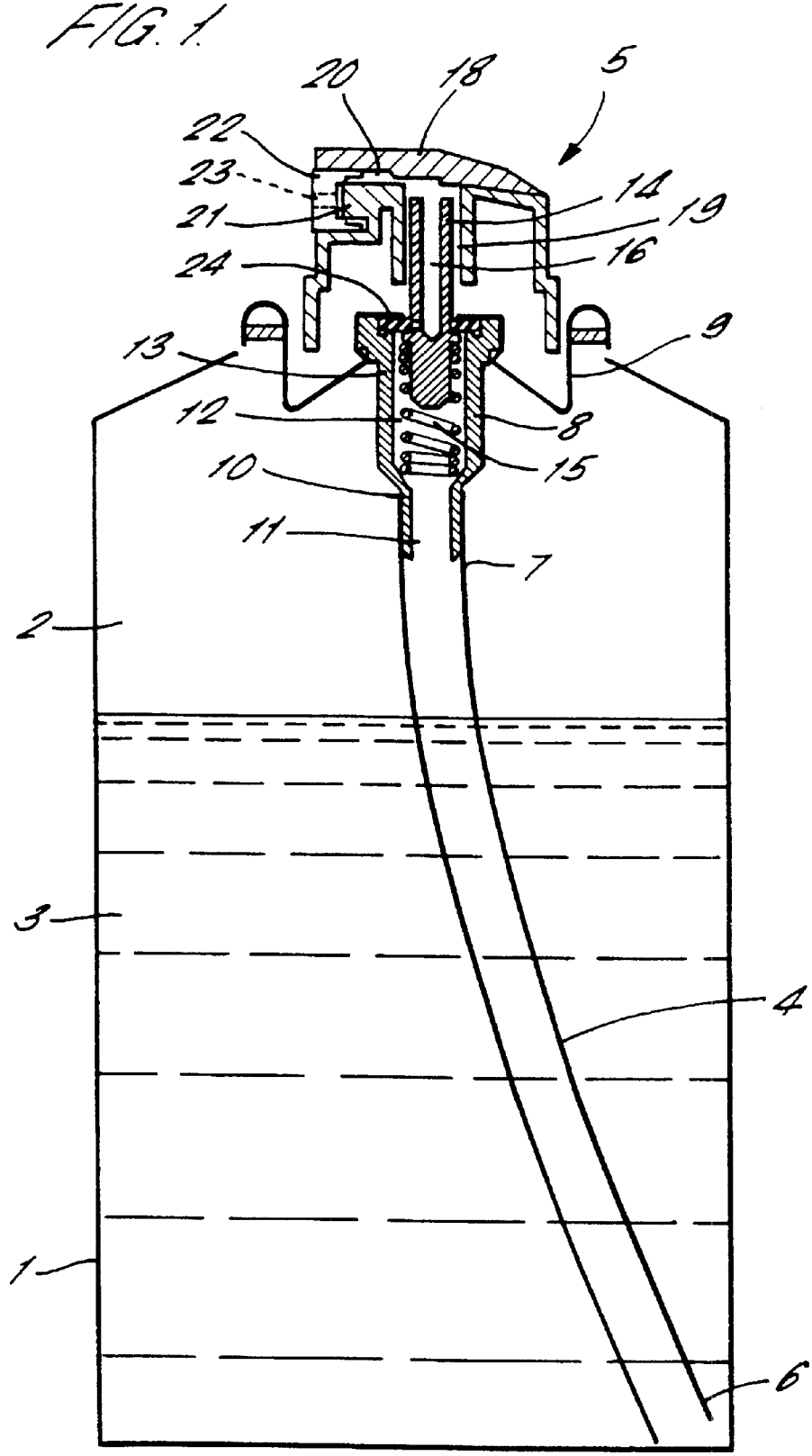
FIG. 1 is a diagrammatic cross section through an aerosol spray apparatus in accordance with the invention.
Figure 2:
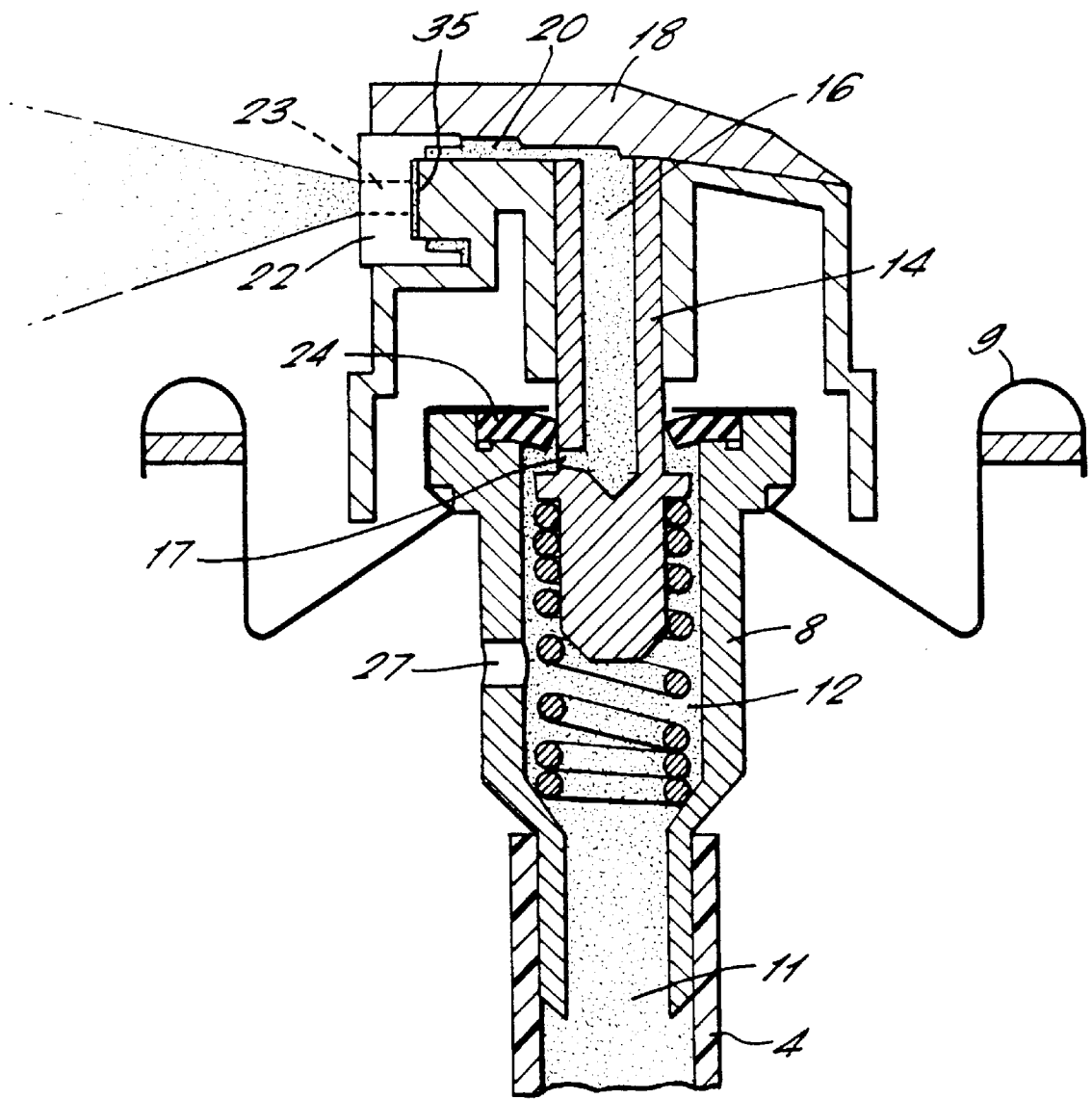
FIG. 2 is a diagrammatic cross section through the valve assembly of the apparatus of FIG. 1.

It is preferred that the unipolar charge which is imparted to the liquid droplets is generated solely by the interaction between the liquid within the spray device and the spray device itself as the liquid is sprayed therefrom. In particular, it is preferred that the manner in which a unipolar charge is imparted to the liquid droplets does not rely even partly upon the connection of the spray device to any external charge inducing device, such as a source of relatively high voltage, or any internal charge inducing device, such as a battery. With such an arrangement, the aerosol spray device is entirely self-contained making it suitable for use both in industrial, institutional and domestic situations.

Preferably, the spray device is a domestic pressure-spraying device devoid of any electrical circuitry but which is capable of being hand held. Typically such a device has a capacity in the range of from 10 ml to 2000 ml and can be actuated by hand, or by an automatic actuating mechanism. A particularly preferred domestic device is a hand-held aerosol can.

Preferably, therefore the droplet charge to mass ratio of at least $+/-1\times10^{-4}$ C/kg is imparted to the liquid droplets as a result of the use of an aerosol spray device with at least one of the features of the material of the actuator, the size and shape of the orifice of the actuator, the diameter of the dip tube, the characteristics of the valve and the formulation of the allergen denaturing or allergen deactivating composition contained within the aerosol device being chosen in order to achieve the said droplet charge to mass ratio by double layer charging imparting the unipolar charge to the droplets during the actual spraying of the liquid droplets from the orifice of the aerosol spray device.

As a result of the method of the present invention there is an active targeting of allergen particles by means of the denaturant or deactivant forming part of the aerosol spray. As a result there is a perceived and actual reduction in allergenic responses due to the increase of the precipitation and deactivation of the allergen from its airborne active condition.

This result is achieved because of the unipolar charge imparted to the liquid droplets of the aerosol spray. This charge has two effects. The individual droplets are attracted to the allergen particles and, since all of the droplets carry the same polarity charge, they are repelled one from other.

Accordingly, there is little or no coalescence of the droplets and, rather, they tend to spread out to a great extent as compared to uncharged droplets. In addition, if the repulsive forces from the charge within the droplets are greater than the surface tension force of the droplets, the charged droplets are caused to fragment into a plurality of smaller charged droplets (exceeding the Rayleigh limit). This process continues until either the two opposing forces are equalised or the droplet has fully evaporated.

Allergen particles are normally electrically isolated from their surroundings and will typically be at a potential which is the same as that of their surroundings. An isolated allergen particle within a cloud of electrically charged liquid droplets thus is likely to cause a distortion in the configuration of the electrical field generated by the droplets so that the attraction of the droplets onto the allergen particle will be enhanced. In effect, the allergen particles are targeted by the liquid droplets.

An example of an allergen denaturant is tannic acid, the use of which is described in U.S. Pat. No. 4,806,526.

Many allergen deactivants are specific to the type of dust mite allergen being treated. For example an effective Der-f allergen deactivant may not work effectively as a Der-p allergen deactivant. Various deactivants for treating Der-f and/or Der-p allergens are described in WO 99/15208.

Examples of deactivants for Der-f and/or Der-p allergens are cedarwood oil, hexadecyltrimethylammonium chloride, aluminum chlorohydrate, 1-propoxypropanol-2, polyquaternium-10, silica gel, propylene glycol alginate, ammonium sulphate, hinokitiol, L-ascorbic acid, immobilised tannic acid, chlorohexidine, maleic anhydride, hinoki oil, a composite of AgCl and $TiO_2$, diazolidinyl urea, 6-isopropyl-m-cresol, a compound of formula I (I)

a compound of formula II (II)

a polymeric dialdehyde containing two or more of a recurring unit of the formula III (III)

where n=2 to 200, urea, cyclodextrin, hydrogenated hop oil, polyvinylpyrrolidone, N-methylpyrrolidone, the sodium salt of anthraquinone, potassium thioglycolate or glutaraldehyde.

The liquid composition which is sprayed into the air using the aerosol spray device is preferably a water and hydrocarbon mixture, or emulsion, or a liquid which is converted into an emulsion by shaking the spraying device before use, or during the spraying process. An example of a composition which could be prepared in a form suitable for spraying in accordance with the method of the invention is a composition based on U.S. Pat. No. 4,806,526.

Whilst all liquid aerosols are known to carry a net negative or positive charge as a result of double layer charging, or the fragmentation of liquid droplets, the charge imparted to droplets of liquid sprayed from standard devices is only of the order of $+/-1\times10^{-8}$ to $1\times10^{-5}$ C/kg.

This invention relies on combining various characteristics of the design of an aerosol spray system so as to increase the charging of the liquid as it is sprayed from the aerosol spray device.

A typical aerosol spray device comprises:
1. An aerosol can containing the composition to be sprayed from the device and a liquid or gaseous propellant;
2. A dip tube extending into the can, the upper end of the dip tube being connected to a valve;
3. An actuator situated above the valve which is capable of being depressed in order to operate the valve; and
4. An insert provided in the actuator comprising an orifice from which the composition is sprayed.

A preferred aerosol spray device is described in WO 97/12227.

It is possible to impart higher charges to the liquid droplets by choosing aspects of the aerosol device including the material, shape and dimensions of the actuator, the actuator insert, the valve and the dip tube and the characteristics of the liquid which is to be sprayed, so that the required level of charge is generated as the liquid is dispersed as droplets.

A number of characteristics of the aerosol system increase double layer charging and charge exchange between the liquid formulation and the surfaces of the aerosol system. Such increases are brought about by factors which may increase the turbulence of the flow through the system, and increase the frequency and velocity of contact between the liquid and the internal surfaces of the container and valve and actuator system.

By way of example, characteristics of the actuator can be optimised to increase the charge levels on the liquid sprayed from the container. A smaller orifice in the actuator insert, of a size of 0.45 mm or less, increases the charge levels of the liquid sprayed through the actuator. The choice of material for the actuator can also increase the charge levels on the liquid sprayed from the device with material such as nylon, polyester, acetal, PVC and polypropylene tending to increase the charge levels. The geometry of the orifice in the insert can be optimised to increase the charge levels on the liquid as it is sprayed through the actuator. Inserts which promote the mechanical break-up of the liquid give better charging.

The actuator insert of the spray device may be formed from a conducting, insulating, semi-conducting or static-dissipative material.

The characteristics of the dip tube can be optimised to increase charge levels in the liquid sprayed from the container. A narrow dip tube, of for example about 1.27 mm internal diameter, increases the charge levels on the liquid, and the dip tube material can also be changed to increase charge.

Valve characteristics can be selected which increase the charge to mass ratio of the liquid product as it is sprayed from the container. A small tailpiece orifice in the housing, of about 0.65 mm, increase product charge to mass ratio during spraying. A reduced number of holes in the stem, for example 2×0.50 mm, also increases product charge during spray. The presence of a vapour phase tap helps to maximise the charge levels, a larger orifice vapour phase tap of, for example, about 0.50 mm to 1.0 mm generally giving higher charge levels.

Changes in the product formulation can also affect charging levels. A formulation containing a mixture of hydrocarbon and water, or an emulsion of an immiscible hydrocarbon and water, will carry a higher charge to mass ratio when sprayed from the aerosol device than either a water alone or hydrocarbon alone formulation.

It is preferred that an allergen neutralising composition of use in the present invention comprises an oil phase, an aqueous phase, a surfactant an allergen denaturant or allergen deactivant and a propellant.

Preferably the oil phase includes a $C_9$–$C_{12}$ hydrocarbon which is preferably present in the composition in the amount of from 2 to 10% w/w.

Preferably the surfactant is glyceryl oleate or a polyglycerol oleate, preferably present in the composition in an amount of from 0.1 to 1.0% w/w.

Preferably the propellant is liquified petroleum gas (LPG) which is preferably butane, optionally in admixture with propane. The propellant may be present in an amount of from 10 to 90% w/w depending upon whether the composition is intended for spraying as a "wet" or as a "dry" composition. For a "wet" composition, the propellant is preferably present in an amount of from 20 to 50% w/w, more preferably in an amount of from 30 to 40% w/w.

The liquid droplets sprayed from the aerosol spray device will generally have diameter in the range of from 5 to 100 micrometers, with a peak of droplets of about 40 micrometers. The liquid which is sprayed from the aerosol spray device may contain a predetermined amount of a particulate material, for example, fumed silica, or a predetermined amount of a volatile solid material, such as menthol or naphthalene.

The method of the present invention, in addition to neutralising allergens also accelerates the natural process of precipitation of airborne particles by indirect charging of the particles, thereby enabling the air quality to be improved quickly and conveniently.

A can for a typical spray device is formed of aluminum or lacquered or unlacquered tin plate or the like. The actuator insert may be formed of, for instance, acetal resin. The valve stem lateral opening may typically be in the form of two apertures of diameters 0.51 mm.

The present invention will now be described, by way of example only, with reference to the to drawings.

Referring to FIGS. 1 and 2, an aerosol spray device in accordance with the invention is shown. It comprises a can 1, formed of aluminum or lacquered or unlacquered tin plate or the like in conventional manner, defining a reservoir 2 for a liquid 3 having a conductivity such that droplets of the liquid can carry an appropriate electrostatic charge. Also located in the can is a gas under pressure which is capable of forcing the liquid 3 out of the can 1 via a conduit system comprising a dip tube 4 and a valve and actuator assembly 5. The dip tube 4 includes one end 6 which terminates at a bottom peripheral part of the can 1 and another end 7 which is connected to a tailpiece 8 of the valve assembly. The tailpiece 8 is secured by a mounting assembly 9 fitted in an opening in the top of the can and includes a lower portion 10 defining a tailpiece orifice 11 to which end 7 of the dip tube 4 is connected. The tailpiece includes a bore 12 of relatively narrow diameter at lower portion 11 and a relatively wider diameter at its upper portion 13. The valve assembly also includes a stem pipe 14 mounted within the bore 12 of the tailpiece and arranged to be axially displaced within the bore 12 against the action of spring 15. The valve stem 14 includes an internal bore 16 having one or more lateral openings (stem holes) 17 (see FIG. 2). The valve assembly includes an actuator 18 having a central bore 19 which accommodates the valve stem 14 such that the bore 16 of the stem pipe 14 is in communication with bore 19 of the actuator. A passage 20 in the actuator extending perpendicularly to the bore 19 links the bore 19 with a recess including a post 21 on which is mounted a spraying head in the form of an insert 22 including a bore 23 which is in communication with the passage 20.

A ring 24 of elastomeric material is provided between the outer surface of the valve stem 14 and, ordinarily, this sealing ring closes the lateral opening 17 in the valve stem 14. The construction of the valve assembly is such that when the actuator 18 is manually depressed, it urges the valve stem 14 downwards against the action of the spring 15 as shown in FIG. 2 so that the sealing ring 24 no longer closes the lateral opening 17. In this position, a path is provided from the reservoir 2 to the bore 23 of the spraying head so that liquid can be forced, under the pressure of the gas in the can, to the spraying head via a conduit system comprising the dip tube 4, the tailpiece bore 12, the valve stem bore 16, the actuator bore 19 and the passage 20.

An orifice 27 (not shown in FIG. 1) is provided in the wall of the tailpiece 8 and constitutes a vapour phase tap whereby the gas pressure in the reservoir 2 can act directly on the liquid flowing through the valve assembly. This increases the turbulence of the liquid. It has been found that an increased charge is provided if the diameter of the orifice 27 is at least 0.76 mm.

Preferably the lateral opening 17 linking the valve stem bore 16 to the tailpiece bore 12 is in the form of two orifices each having a diameter of not more than 0.51 mm to enhance electrostatic charge generation. Further, the diameter of the dip tube 4 is preferably as small as possible, for example, 1.2 mm, in order to increase the charge imparted to the liquid. Also, charge generation is enhanced if the diameter of the tailpiece orifice 11 is as small as possible e.g. not more than about 0.64 mm.

Referring now to FIG. 3, there is shown on an increased scale, a cross section through the actuator insert of the apparatus of FIGS. 1 and 2. For simplicity, the bore 23 is shown as a single cylindrical aperture in this Figure. However, the bore 23 preferably has the configuration, for instance, shown in FIG. 4. The apertures of the bore 23 are denoted by reference numeral 31 and the aperture-defining portions of the bore are denoted by reference numeral 30. The total peripheral length of the aperture-defining portions at the bore outlet is denoted by L (in mm) and a̲ is the total area of the aperture at the bore outlet (in $mm^2$) and the values for L and a are as indicated in FIG. 4. L/a̲ exceeds 8 and this condition has been found to be particularly conductive to charge development because it signifies an increased contact area between the actuator insert and the liquid passing there through.

Many different configurations can be adopted in order to produce a high L/a̲ ratio without the cross-sectional area a being reduced to a value which would allow only low liquid flow rates. Thus, for example it is possible to use actuator insert bore configurations (i) wherein the bore outlet comprises a plurality of segment-like apertures (with or without a central aperture); (ii) wherein the outlet comprises a plurality of sector-like apertures; (iii) wherein the aperture together form an outlet in the form of a grill or grid; (iv) wherein the outlet is generally cruciform; (v) wherein the apertures together define an outlet in the form of concentric rings; and combinations of these configurations. Particularly preferred are actuator insert bore configurations wherein a tongue like portion protrudes into the liquid flow stream and can be vibrated thereby. This vibrational property may cause turbulent flow and enhanced electrostatic charge separation of the double layer, allowing more charge to move into the bulk of the liquid.

Referring now to FIG. 5, there is shown a plan view of one possible configuration of swirl chamber 35 of the actuator insert 22. The swirl chamber includes four lateral channels 36 equally spaced and tangential to a central area 37 surrounding the bore 23. In use, the liquid driven from the reservoir 2 by the gas under pressure travels along passage 20 and strikes the channels 36 normal to the longitudinal axis of the channels. The arrangement of the channels is such that the liquid tends to follow a circular motion prior to entering the central area 37 and thence the bore 23. As a consequence, the liquid is subjected to substantial turbulence which enhances the electrostatic charge in the liquid.

The following Examples illustrate the invention:

EXAMPLE 1

The concentration of allergen (for example Der p1, Der f1, Fel d1 or Bla g1) in an artificially created aerosol of dust particles (of domestic origin) was quantified, and compared with the configuration following treatment of the dust cloud with a charged liquid aerosol containing a neutralising agent and an identical charged liquid aerosol not containing a neutralising agent. The dust cloud was generated in a test chamber of 2.2 m$^3$ by dispersing 2.0 g of house dust with compressed air. 2.0 g of liquid aerosol (either with or without the neutralising agent) were sprayed into the centre of the dust cloud, and air sampling commenced immediately. Air was sampled at a rate of 18 liters per minute for 5 minutes, through a glass fibre filter paper supported in an in-line filter holder (German laboratories) to collect airborne particles. Allergen was eluted from these collection papers in 1 ml of 10% BSA PBS-T (Phosphate buffered Saline with 0.05% Tween and 10% Bovine Serum Albumen) overnight. The filter paper was then removed and the remaining solution centrifuged for 5 minutes at 13,000 rpm. The supernatant, containing the allergen in solution, was decanted into a clean container. Control measurements were taken by sampling the dust cloud without treating it with liquid aerosol. A minimum of 5 replicates were performed for the control and for treatment with the charged aerosol containing a neutralising agent and the equivalent aerosol without the neutralising agent. Allergen concentrations in the solutions collected were assayed using standard ELISA (Enzyme Linked ImmunoSorbent Assay) methods.

The aerosol formulation containing a neutralising agent was produced from the following ingredients:

Ethyl Alcohol (30% v/v)
Water (59% v/v)
Benzyl Alcohol (10% v/v)
Tannic Acid (1% w/v)

The mixture was introduced into a conventional aerosol can.

The can was pressurized using compressed air to achieve a pressure of 130 psi within the can.

The charge level on droplets emitted from this spray can was artificially raised to a charge to mass ratio of $-1\times10^{-4}$ C/kg by supplying $-10$ kv charge to the seam of the can from a high voltage power supply. A flow rate of approximately 1.5 g/sec was obtained. The droplets became rapidly dispersed in the air.

The above-described aerosol spray device was compared with a standard, known aerosol spray device loaded with the same aerosol formulation. When used to counteract allergens in a room according to the protocol as described above, it was found that the amount of spraying required was significantly less with the above-described device compared with the standard, known device.

EXAMPLE 2

The depletion rate of dust particles in an actinically created dust cloud containing a quantified concentration of allergen was quantified using an air particle counter (APC 300A, Malvern Instruments, Malvern, UK). The rate of depletion occurring through natural processes alone was compared with the rate after treatment of the dust cloud with a charged liquid aerosol composition containing an allergen denaturant (charge-to-mass ratio of $-1.4\times10^{-4}$ C/kg$^{-1}$) sprayed from a hand-held pressure-pack dispenser, and an equivalent liquid aerosol which was not charged (charge-to-mass ratio of $-1.3\times10^{-6}$ C/kg$^{-1}$). A cloud of dust particles (of domestic origin) was created in a test chamber 2.2 m$^3$, by dispersing 2.0 g of dust with compressed air. The concentration of particles in this cloud over a 14 minute period was quantified using the air particle counter, and gave a rate for the natural depletion rate for this dust. To quantify the effect of the charged and uncharged liquid aerosol sprays on the concentration of dust particles a 2.0 g spray of one of these sprays was made into the center of the artificial dust cloud, immediately following a first measurement of particle concentration. Subsequent measurements of dust concentration reflected the particle depletion achieved by the liquid aerosol spray. A minimum of 5 replicates were conducted for the natural rate of particle settling, and for depletion caused by the uncharged and the charged liquid aerosol spray.

Figure 6:
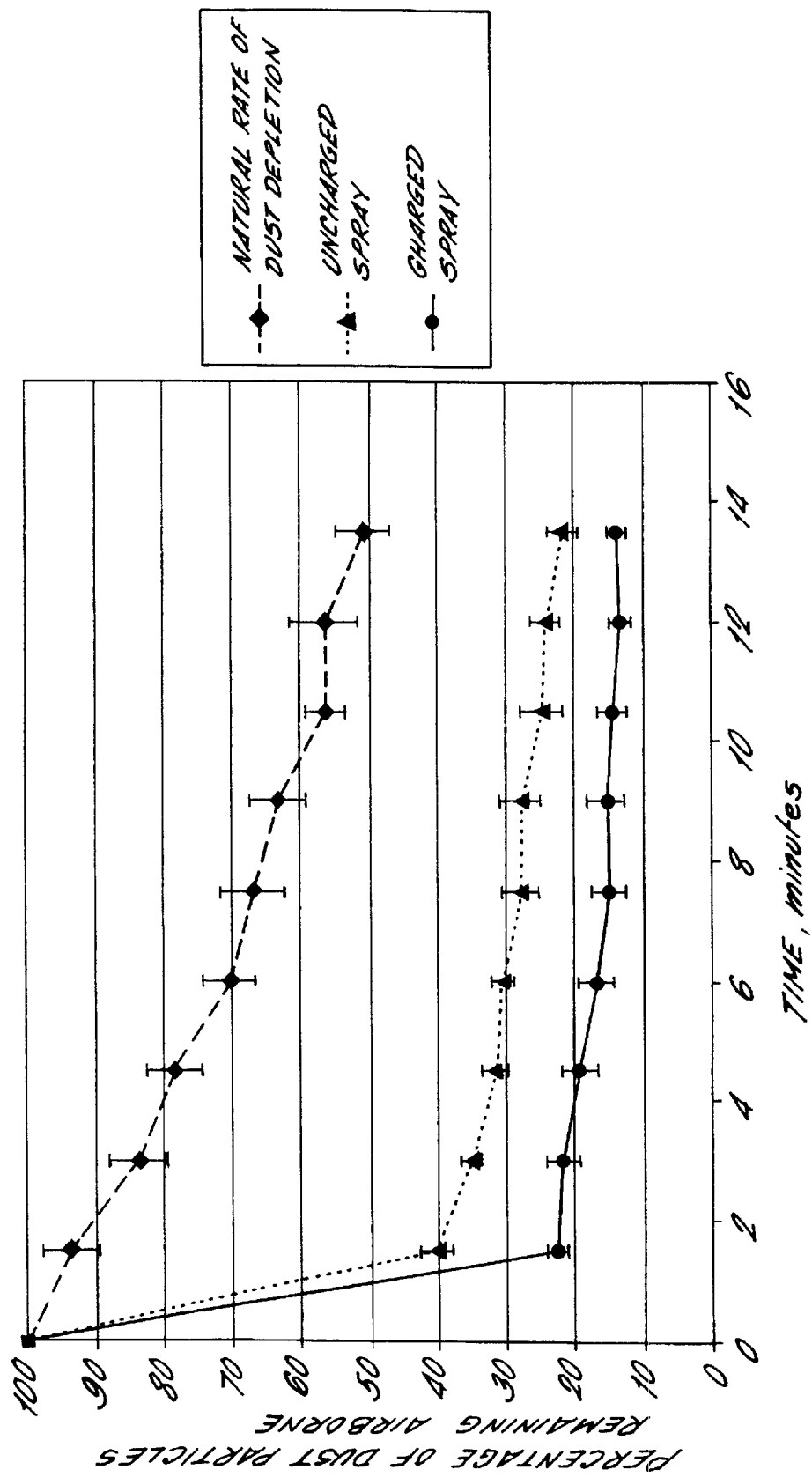
FIG. 6 illustrates the method of the invention as described in Example 2 in relation to the rate of precipitation of dust particles containing allergens.

Typical results are shown in FIG. 6 for the percentage of 1 to 2 micron diameter particles remaining airborne. The rate at which dust particles settle due to natural processes alone was quite steady and slow. Liquid aerosol sprays, generated by hand-held pressure-pack devices caused the depletion of 60% of the particles within 90 seconds. Charged liquid aerosol sprays depleted almost 80% of particles within 90 seconds. The improved particle depletion and allergen denaturation achieved when the liquid aerosol was charged over that achieved by the uncharged liquid aerosol was statistically significant ($p<0.05$).

What is claimed is:

1. A method of denaturing or deactivating an airborne allergen comprising directing at the airborne source of the allergen liquid droplets from a spray device containing a liquid composition which includes an allergen denaturant or allergen deactivate, a unipolar charge being imparted to the liquid droplets by double layer charging during the spraying of the liquid droplets by the spray device, the unipolar charge being at a level such that said droplets have a charge to mass ratio of at least $\pm 1\times10^{-4}$ C/kg, whereby said allergen is denatured or deactivated whilst airborne and the denatured or deactivated allergen precipitates as a result of mutual repulsion of the charged droplets.

2. A method as claimed in claim 1 wherein the spray device is an aerosol spray device.

3. A method as claimed in claim 2 wherein the liquid composition is an emulsion.

4. A method as claimed in claim 3 wherein the liquid droplets have a diameter in the range of from 5 to 100 micrometers.

5. A method as claimed claim 4 wherein the composition includes an allergen denaturant or deactivant effective against Der-f, Der-p, Fel-d and/or Bla-g allergens.

6. A method as claimed in claim 4 wherein the unipolar charge is imparted to the liquid droplets solely by the interaction between the liquid and the spray device, without any charge being imparted thereto from an internal or external charge inducing device.

7. A method as claimed in claim 6 wherein the required droplet charge to mass ratio is imparted to the liquid droplets as a result of the use of an aerosol spray device with at least one of the features of:

(a) the material of the actuator, (b) the size and shape of the orifice of the actuator, (c) the diameter of the dip tube, (d) the characteristics of the valve, and (e) the formulation of the allergen denaturing or allergen deactivating composition contained within the aerosol device being chosen in order to achieve said droplet charge to mass ratio by double layer charging imparting the unipolar charge to the droplets during the actual spraying of the liquid droplets from the orifice of the aerosol spray device.

8. A method as claimed in claim 7 wherein the liquid composition comprises an oil phase, an aqueous phase, a surfactant, an allergen denaturant or allergen deactivant and a propellant.

9. A method as claim in claim 8 wherein the oil phase includes a $C_9$–$C_{12}$ hydrocarbon.

10. A method as claimed in claim 9 wherein the $C_9$–$C_{12}$ hydrocarbon is present in the composition in an amount of from 2 to 10% w/w.

11. A method as claimed in claim 8 wherein the surfactant is glyceryl oleate or a polyglycerol oleate.

12. A method as claimed in claim 11 wherein the surfactant is present in the composition in an amount of from 0.1 to 1.0% w/w.

13. A method as claimed in claim 8 wherein the propellant is liquified petroleum gas or compressed gas.

14. A method as claimed in claim 13 wherein the propellant is present in the composition in an amount of from 20 to 50% w/w.

15. A method as claimed in claim 5 wherein the composition includes an allergen denaturant for Der-f and/or Der-p allergens.

16. A method as claimed in claim 15 wherein the allergen denaturant and is selected from the group consisting of cedarwood oil, hexadecyltrimethylammonium chloride, aluminum chlorohydrate, 1-propoxypropanol-2, polyquaternium-10, silica gel, propylene glycol alginate, ammonium sulphate, hinokitiol, L-ascorbic acid, immobilized tannic acid, chlorohexidine, maleic anhydride, hinoki oil, a composite of AgCl and $TiO_2$, diazolidinyl urea, 6-isopropyl-m-cresol, a compound of formula I (I)

a compound of formula II (II)

a polymeric dialdehyde containing two or more of a recurring unit of the formula III (III)

where n=2 to 200, urea, cyclodextrin, hydrogenated hop oil, polyvinylpyrrolidone, N-methylpyrrolidone, the sodium salt of anthraquinone, potassium thioglycolate or glutaraldehyde.

* * * * *

UNITED STATES PATENT AND TRADEMARK OFFICE
CERTIFICATE OF CORRECTION

PATENT NO. : 6,482,357 B1
DATED : November 19, 2002
INVENTOR(S) : Rodney Thomas Fox et al.

It is certified that error appears in the above-identified patent and that said Letters Patent is hereby corrected as shown below:

<u>Title page,</u>
Item [73], Assignee, should read as follows:
-- [73]   Assignee:       Reckitt Benckiser (UK) Limited, Slough (GB)
                          and
                          University of Southampton, Southampton, (GB) --

Signed and Sealed this

Twenty-ninth Day of April, 2003

JAMES E. ROGAN
*Director of the United States Patent and Trademark Office*